(12) United States Patent
Chorghade et al.

(10) Patent No.: US 6,846,958 B2
(45) Date of Patent: Jan. 25, 2005

(54) SYNTHESIS OF BENZIMIDATE FROM BENZOIC ACID

(75) Inventors: Mukund S. Chorghade, Natick, MA (US); Mukund K. Gurjar, Pune Maharashtra (IN); Joseph Cherian, Kerala (IN)

(73) Assignee: Genzyme Corporation, Cambridge, MA (US)

( * ) Notice: Subject to any disclaimer, the term of this patent is extended or adjusted under 35 U.S.C. 154(b) by 74 days.

(21) Appl. No.: 10/439,342

(22) Filed: May 15, 2003

(65) Prior Publication Data

US 2003/0236426 A1 Dec. 25, 2003

Related U.S. Application Data

(60) Provisional application No. 60/392,833, filed on Jun. 27, 2002, provisional application No. 60/381,021, filed on May 15, 2002, provisional application No. 60/381,012, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, and provisional application No. 60/380,909, filed on May 15, 2002.

(51) Int. Cl.$^7$ ............................................. C07C 217/46

(52) U.S. Cl. ........................................................ 564/346

(58) Field of Search .......................................... 564/346

(56) References Cited

U.S. PATENT DOCUMENTS

| | | | |
|---|---|---|---|
| 4,406,905 | A | 9/1983 | Zähner et al. |
| 5,554,753 | A | 9/1996 | O'Donnell et al. |
| 5,840,739 | A | 11/1998 | Bergeron, Jr. |
| 5,872,259 | A | 2/1999 | Reuter |
| 5,929,232 | A | 7/1999 | Jacobsen et al. |
| 6,083,966 | A | 7/2000 | Bergeron, Jr. |
| 6,159,983 | A | 12/2000 | Bergeron, Jr. |
| 6,383,233 | B1 | 5/2002 | Reuter |
| 6,428,583 | B1 | 8/2002 | Reuter |
| 6,521,652 | B1 | 2/2003 | Bergeron |
| 6,525,080 | B1 | 2/2003 | Bergeron |
| 6,559,315 | B1 | 5/2003 | Bergeron |
| 2003/0088105 | A1 | 5/2003 | Krich et al. |
| 2003/0220504 | A1 | 11/2003 | Chorghade et al. |
| 2003/0225287 | A1 | 12/2003 | Chorghade et al. |
| 2003/0229231 | A1 | 12/2003 | Chorghade et al. |
| 2003/0236404 | A1 | 12/2003 | Gimi et al. |
| 2003/0236434 | A1 | 12/2003 | Gimi et al. |
| 2003/0236435 | A1 | 12/2003 | Gimi et al. |
| 2004/0002613 | A1 | 1/2004 | Chorghade et al. |
| 2004/0006224 | A1 | 1/2004 | Chorghade et al. |
| 2004/0024224 | A1 | 2/2004 | Chorghade et al. |

FOREIGN PATENT DOCUMENTS

| | | |
|---|---|---|
| DE | 2020866 | 11/1971 |
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/12493 | 3/2000 |
| WO | WO 00/16763 | 3/2000 |
| WO | WO 01/51477 A1 | 7/2001 |

OTHER PUBLICATIONS

Meyers et al, J. Am. Chem. Soc., 1987, 109, 5446–5452.*
Bergeron, R.J., et al., "The Desferrithiocin Pharmacophore," *J. Med. Chem.*, 37: 1411–1417 (1994).
Bergeron, R.J., et al., "Effects of C–4 Stereochemistry and C–4' Hydroxylation on the Iron Clearing Efficiency and Toxicity of Desferrithiocin Analogues," *J. Med. Chem.*, 42: 2432–2440 (1999).
Bergeron, R. J., et al., "Synthesis and Biological Evaluation of Naphthyldesferrithiocin Iron Chelators," *J. Med. Chem.* 39:1575–1581 (1996).
Bergeron, R. J., et al., "Pharmacokinetics of Orally Administered Desferrithiocin Analogs in *Cebus Apella* Primates," *Drug Metabol. And Dispos.* 27(12):1496–1498 (1999).
Bergeron, R. J., et al., "Evaluation of Desferrithiocin and Its Synthetic Analogues as Orally Effective Iron Chelators," *J. Med. Chem.* 34:2072–2078 (1991).
Bergeron, R. J., et al., "Evaluation of Desferrithiocin Pharmacophore as a Vector for Hydroxamates," *J. Med. Chem.* 42:2881–2886 (1999).
Bergeron, R. J., et al., "Desazadesmethyldesferrithiocin Analogues as Orally Effective Iron Chelators," *J. Med. Chem.* 42:95–108 (1999).
Bergeron, R. J., et al., "An Investigation of Desferrithiocin Metabolism," *J. Med. Chem.* 37:2889–2895 (1994).
Bergeron, R. J., et al., "A Comparative Study of the Iron-Clearing Properties of Desferrithiocin Analogues With Desferrioxamine B in a *Cebus* Monkey Model," *Blood* 81(8):2166–2173 (1993).
Mulqueen, G. C., et al., "Synthesis of the Thiazoline–based Siderophore (S)–Desferrithiocin," *Tetrahedron*, 49(24):5359–5364 (1993).
O'Donnell, M. J., et al., "α–Methyl Amino Acids by Catalytic Phase–Transfer Aklylations," *Tetrahedron Letters*, 23(41):4259–4262 (1982).

* cited by examiner

*Primary Examiner*—Zinna Northington Davis
(74) *Attorney, Agent, or Firm*—Hamilton, Brook, Smith & Reynolds, P.C.

(57) ABSTRACT

Benzimidates can be reacted with a large number of nucleophiles, leading to a wide variety of products. The present invention discloses a facile synthesis for ethyl 2,4-dihydroxybenzimidate, and ethers and diethers thereof, from 2,4-dihydroxybenzoic acid or 2,4-dibenzyloxybenzoic acid. The present invention also discloses a method of preparing a class of iron chelating agents related to desferrithiocin, all of which contain a thiazoline ring. In this method, 2,4-dihydroxybenzonitrile is condensed with (S)-2-methylcysteine.

13 Claims, No Drawings

SYNTHESIS OF BENZIMIDATE FROM BENZOIC ACID

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

An imidate moiety is strongly electrophilic, and as such, represents an important functional group in organic synthesis. The imidate moiety can be transformed into a wide variety of products, by virtue of undergoing reaction with a large number of nucleophiles. In addition, the imidate moiety can serve as a free radical scavenger. For example, ethyl 3,4,5-trihydroxybenzimidate blocks free radical generation from NADPH oxidase. This free radical scavenging activity decreases the amount of tissue damage, such as limiting damage to the heart following an infarction or other ischemic episode.

The use of aryl imidates in the preparation of thiazoles, or when reduced, thiazolines and thiazolidines, is of particular interest. Compounds such as desferrithiocin and structural analogues contain a thiazoline ring, and these compounds represent an advance in iron chelation therapy for subjects suffering from iron overload diseases. Present therapeutic agents such as desferrioxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues.

Unfortunately, ethyl 2,4-dihydroxybenzimidate, which is a precursor to the potent, less toxic form of desferrithiocin known as 4'-hydroxydesazadesferrithiocin, remains a synthetic challenge. At this time, alkyl 2,4-dihydroxybenzimidates are not commercially available. Therefore, there is a need for novel methods of producing alkyl 2,4-dihydroxybenzimidate at a reasonable cost.

SUMMARY OF THE INVENTION

In one embodiment, the present invention is a method of preparing a substituted benzimidate represented by Structural Formula (I):

(I)

wherein:
   $R_1$ and $R_2$ are each independently —H, a substituted or unsubstituted alkyl group, a substituted or unsubstituted aryl group, or a substituted or unsubstituted arylalkyl group; and
   $R_3$ is a substituted or unsubstituted alkyl group; comprising the steps of:

a.) reacting a chlorinating agent and a disubstituted benzoic acid represented by Structural Formula (II):

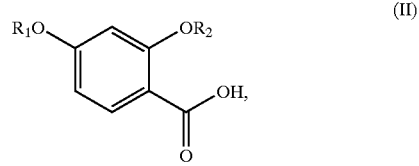

(II)

wherein $R_1$ and $R_2$ are as defined above, thereby forming a substituted benzoyl chloride represented by Structural Formula (III):

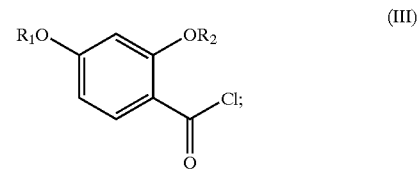

(III)

b.) reacting the substituted benzoyl chloride with ammonia or a salt thereof, thereby forming a substituted benzamide represented by Strucutural Formula (IV):

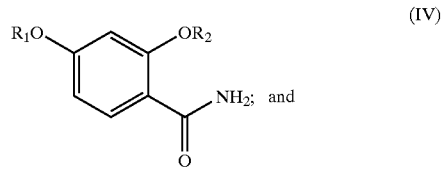

(IV)

c.) reacting the substituted benzamide with a trialkyloxonium hexafluorophosphate of the formula $(R_3)_3OPF_6$, wherein $R_3$ is as represented above, thereby forming the substituted benzimidate represented by Structural Formula (I).

In another embodiment, the present invention is a method of preparing a 2,4-dihydroxybenzimidate represented by Structural Formula (V):

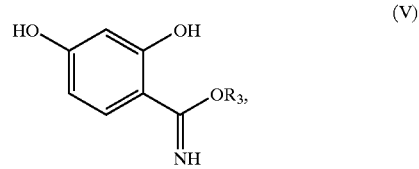

(V)

wherein $R_3$ is a substituted or unsubstituted alkyl group; comprising the steps of:
   a.) protecting 2,4-dihydroxybenzoic acid with protecting groups, thereby forming protected benzoic acid represented by Structural Formula (II):

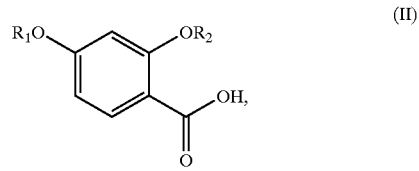

(II)

wherein $R_1$ and $R_2$ are each independently a substituted or unsubstituted alkyl group, a substituted or unsubstituted aryl group, or a substituted or unsubstituted arylalkyl group;

b.) reacting a chlorinating agent and the protected benzoic acid, wherein $R_1$ and $R_2$ are as defined above, thereby forming a protected benzoyl chloride represented by Structural Formula (III):

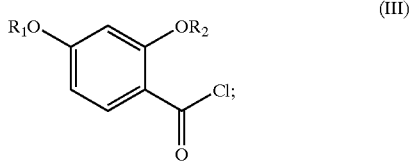

(III)

c.) reacting the protected benzoyl chloride with ammonia or a salt thereof, thereby forming a protected benzamide represented by Structural Formula (IV):

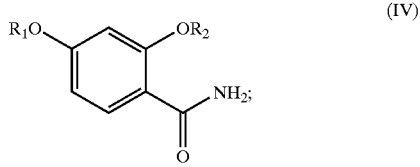

(IV)

d.) reacting the protected benzamide with a trialkyloxonium hexafluorophosphate of the formula $(R_3)_3OPF_6$, wherein $R_3$ is as defined above, thereby forming a protected benzimidate represented by Structural Formula (VI):

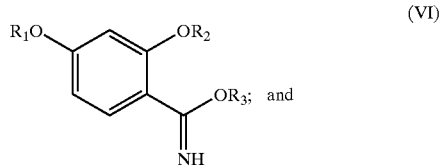

(VI)

e.) deprotecting the protected benzimidate, thereby forming the 2,4-dihydroxybenzimidate.

In another embodiment, the present invention is a method of preparing a compound represented by Structural Formula (VII):

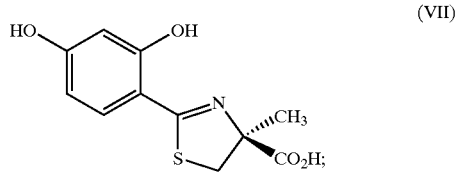

(VII)

which is prepared by coupling (S)-2-methylcysteine and a 2,4-dihydroxybenzimidate, the preparation of which is described above.

Advantages of the present invention include the facile synthesis of an alkyl 2,4-dihydroxybenzimidate from 2,4-dihydroxybenzoic acid, an inexpensive and readily available starting material. An alkyl 2,4-dihydroxybenzimidate (specifically ethyl 2,4-dihydroxybenzimidate) prepared by the method of the present invention can be coupled to (S)-2-methylcysteine to form 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

A useful and efficient method of preparing ethyl 2,4-dihydroxybenzimidate, or an ether or diether thereof, involves amidating 2,4-dihydroxybenzoic acid or a diether thereof, such as 2,4-dibenzyloxybenzaldehyde. The amide is typically reacted with a trialkyloxonium salt to form an imidate. Functional groups protecting hydroxyl groups, such as benzyl groups, can be removed, for example, by hydrogenation.

In examples where $R_1$ and $R_2$ of Structural Formula (I) are each —H, $R_1$ and $R_2$ can be protected by protecting groups. A preferred protecting group is a substituted or unsubstituted arylalkyl group such as a benzyl group. Protecting groups can be added, for example, by reacting 2,4-dihydroxybenzoic acid, a base, and a benzyl compound substituted with a leaving group (e.g., benzyl tosylate, a benzyl halide such as benzyl chloride or benzyl bromide) in a polar, aprotic solvent (e.g., acetone, acetonitrile, dimethylformamide, dioxane, ethyl acetate, ethyl ether, hexamethylphosphoramide, tetrahydrofuran). Suitable bases include sodium hydride, potassium hydride, sodium amide, potassium amide, and lithium diisopropylamide. In one example, 2,4-dihydroxybenzoic acid is reacted with sodium hydride and benzyl bromide in dimethylformamide to yield a compound with protected hydroxyl and carboxylic acid groups. The carboxylic acid can be deprotected by refluxing the compound in a basic dioxane solution. Suitable bases include sodium hydroxide and potassium hydroxide. The solution is acidified after refluxing. Additional protecting groups can be found, for example, in "Protective Groups in Organic Synthesis, Third Edition," by Peter G. M. Wuts and Theodora W. Greene, Wiley-Interscience, 1999.

The first step of the reaction involves reacting a compound represented by Structural Formula (II):

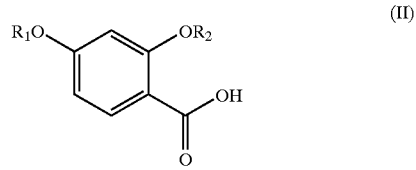

(II)

with a chlorinating agent in a polar, aprotic solvent (as defined above) or a mixture of a polar, aprotic solvent and a nonpolar solvent, in order to form an acid chloride. Suitable chlorinating agents include thionyl chloride, phosphorus trichloride, or, preferably, oxalyl chloride. Suitable nonpolar solvents include pentane, heptane, octane, hexane (s), cyclohexane, carbon tetrachloride, toluene, xylenes, and benzene. Typically, the reaction is carried out at or below 30° C., such as from about −50° C. to about 30° C., about −30° C. to about 25° C., or about 0° C. to about 25° C. If the carboxylic acid is protected (e.g., as a result of protecting the hydroxyl groups), the acid is preferably deprotected prior to reaction with a chlorinating agent.

The acid chloride can be reacted with ammonia or a salt thereof (e.g., $NH_4OH$) to form an amide (e.g., a benzamide). For example, the acid chloride can be reacted with an aqueous ammonia solution in a polar, aprotic solvent such as methylene chloride or another of those listed above to form the amide.

The amide is typically reacted with a trialkyloxonium hexafluorophosphate of the formula $(R_3)_3OPF_6$ to form a benzimidate. Preferred $R_3$ groups are C1–C4 alkyl groups such as methyl, ethyl, propyl, isopropyl, butyl, isobutyl, and t-butyl. Ethyl is an especially preferred $R_3$. In one example, the amide formed above is reacted with triethyloxonium hexafluorophosphate in a polar, aprotic solvent such as methylene chloride to form an ethyl benzimidate.

In examples where $R_1$ and $R_2$ are not each —H in the benzimidate formed above, it may be desirable to cleave $R_1$ and $R_2$ to deprotect hydroxyl groups. A suitable method to deprotect the hydroxyl groups includes reacting the protected benzimidate with hydrogen. For example, a protected benzimidate can be hydrogenated by reacting the benzimidate with 1 atmosphere of hydrogen in the presence of a palladium-carbon catalyst in a polar, protic solvent such as methanol or ethanol. The hydrogenation yields a deprotected benzimidate, such as ethyl 2,4-dihydroxybenzimidate.

Cysteine or a 2-alkylcysteine such as (S)-2-methylcysteine can be coupled with 2,4-dihydroxybenzimidate, or an ether or diether thereof. In a preferred embodiment, (S)-2-methylcysteine is coupled to 2,4-dihydroxybenzimidate to form 4,5-dihydro-2-(2,4-dihydroxyphenyl)-4-methylthiazole-4(S)-carboxylic acid (also known as 4'-hydroxydesazadesferrithiocin).

Syntheses of cysteine and cysteine derivatives suitable for coupling can be found in U.S. application Ser. Nos. 60/381,012, 60/381,021, 60/380,894, 60/380,910, 60/380,880, 60/381,017, 60/380,895 and 60/380,903, filed May 15, 2002, and U.S. application Ser. No. 60/392,833, filed Jun. 27, 2002; the entire teachings of which are incorporated herein by reference.

Typically, coupling of cysteine or a 2-alkylcysteine and a substituted benzimidate includes reacting cysteine (or a related compound) with the substituted benzimidate under basic conditions. Acceptable bases include trimethylamine, triethylamine, triphenylamine, diisopropylamine, diisopropylethylamine, diethylamine, dimethylamine, diphenylamine, DABCO, DBN, and the like. The reaction between the substituted benzimidate and cysteine (or the related compound) results in the thiazoline (or 4,5-dihydrothiazole) containing product.

Compounds synthesized by methods of the present invention can be purified by a method known in the art. For example, compounds of the present invention can be purified by emulsion crystallization.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080, to Raymond J. Bergeron, Jr., the contents of which are incorporated herein by reference. Additional examples can be found in PCT/US93/10936, PCT/US97/04666, and PCT/US99/19691, the contents of which are incorporated by reference.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Alkyl groups can additionally be substituted by an aryl group (e.g. an alkyl group can be substituted with an aromatic group to form an arylalkyl group). A substituted alkyl group can have more than one substituent.

Suitable substituents for aryl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Aryl groups can additionally be substituted by an alkyl or cycloaliphatic group (e.g. an aryl group can be substituted with an alkyl group to form an alkylaryl group such as tolyl). A substituted aryl group can have more than one substituent.

Although a benzamide is preferably reacted with a trialkyloxonium hexafluorophosphate, benzamide can also be reacted with trialkyloxoxium tetrafluoroborate salts.

EXAMPLE 1

2,4-Dihydroxybenzoic acid was reacted with sodium hydride and benzyl bromide in dimethylformamide (DMF) to give a compound protected with benzyl groups at hydroxyl and carboxylic acids moieties in a 91% yield. The benzyl group was removed from the carboxylic acid moiety by refluxing it with 2 N sodium hydroxide in dioxane, followed by acidifying the mixture, to give 2,4-dibenzyloxybenzoic acid in 83% yield.

2,4-Dibenzyloxybenzoic acid was reacted with oxalyl chloride in toluene and DMF at 0–25° C. to give an acid chloride. The acid chloride was reacted with aqueous ammonia in methylene chloride to yield 87% (over 2 steps) of 2,4-dibenzyloxybenzamide. 2,4-Dibenzyloxybenzamide was reacted with triethyloxonium hexafluorophosphate in methylene chloride to yield 69% of ethyl 2,4-dibenzyloxybenzimidate. The ethyl 2,4-dibenzyloxybenzimidate was hydrogenated over a palladium/carbon catalyst with 1 atmosphere of hydrogen gas in ethanol, to yield 75% of ethyl 2,4-dihydroxybenzimidate. The overall yield for the reaction sequence was 34% for six steps.

EXAMPLE 2

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallization was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 3

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4 (S)-carboxylic acid product. $^1$H-NMR showed no significant impurity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a substituted benzimidate represented by Structural Formula (I):

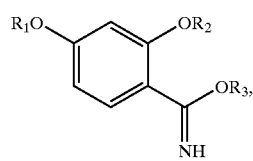

(I)

wherein:

$R_1$ and $R_2$ are each independently —H, a substituted or unsubstituted alkyl group, a substituted or unsubstituted aryl group, or a substituted or unsubstituted arylalkyl group; and $R_3$ is a substituted or unsubstituted alkyl group;

comprising the steps of:

a.) reacting a chlorinating agent and a disubstituted benzoic acid represented by Structural Formula (II):

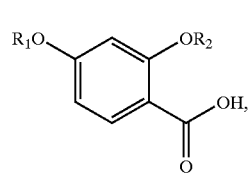

(II)

wherein $R_1$ and $R_2$ are as defined above, thereby forming a substituted benzoyl chloride represented by Structural Formula (III):

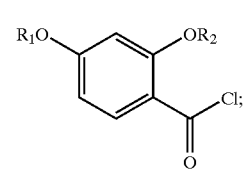

(III)

b.) reacting the substituted benzoyl chloride with ammonia or a salt thereof, thereby forming a substituted benzamide represented by Structural Formula (IV):

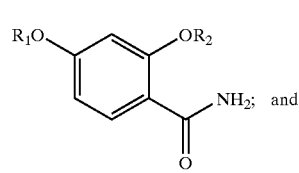

(IV)

and c.) reacting the substituted benzamide with a trialkyloxonium hexafluorophosphate of the formula $(R_3)_3OPF_6$, wherein $R_3$ is as represented above, thereby forming the substituted benzimidate represented by Structural Formula (I).

2. The method of claim 1, wherein $R_1$ and $R_2$ are each substituted or unsubstituted arylalkyl groups.

3. The method of claim 2, wherein $R_1$ and $R_2$ are each a benzyl group.

4. The method of claim 3, wherein $R_3$ is a C1–C4 alkyl group.

5. The method of claim 4, wherein $R_3$ is an ethyl group.

6. The method of claim 5, wherein the chlorinating agent is oxalyl chloride.

7. A method of preparing a 2,4-dihydroxybenzimidate represented by Structural Formula (V):

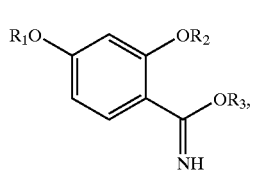

(V)

wherein $R_3$ is a substituted or unsubstituted alkyl group; comprising the steps of:

a.) protecting 2,4-dihydroxybenzoic acid with protecting groups, thereby forming protected benzoic acid represented by Structural Formula (II):

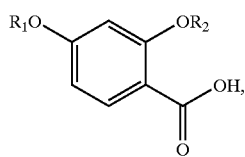

(II)

wherein $R_1$ and $R_2$ are each independently a substituted or unsubstituted alkyl group, a substituted or unsubstituted aryl group, or a substituted or unsubstituted arylalkyl group;

b.) reacting a chlorinating agent and the protected benzoic acid, wherein $R_1$ and $R_2$ are as defined above, thereby forming a protected benzoyl chloride represented by Structural Formula (III):

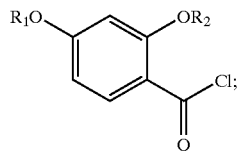

(III)

c.) reacting the protected benzoyl chloride with ammonia or a salt thereof, thereby forming a protected benzamide represented by Strucutural Formula (IV):

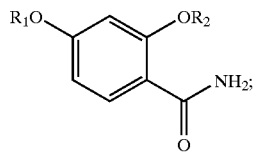

(IV)

d.) reacting the protected benzamide with a trialkyloxonium hexafluorophosphate of the formula $(R_3)_3OPF_6$, wherein $R_3$ is as defined above, thereby forming a protected benzimidate represented by Structural Formula (VI):

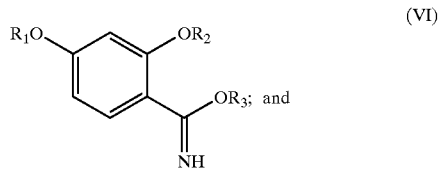

(VI)

e.) deprotecting the protected benzimidate, thereby forming the 2,4-dihydroxybenzimidate.

8. The method of claim 7, wherein $R_3$ is a C1–C4 alkyl group.

9. The method of claim 8, wherein $R_3$ is ethyl.

10. The method of claim 9, wherein $R_1$ and $R_2$ are each substituted or unsubstituted arylalkyl groups.

11. The method of claim 10, wherein $R_1$ and $R_2$ are each benzyl groups.

12. The method of claim 11, wherein the chlorinating agent is oxalyl chloride.

13. The method of claim 12, wherein deprotecting the protected benzimidate comprises reacting said protected benzimidate with hydrogen in the presence of a palladium-carbon catalyst.

* * * * *

UNITED STATES PATENT AND TRADEMARK OFFICE
CERTIFICATE OF CORRECTION

PATENT NO. : 6,846,958 B2 Page 1 of 1
DATED : January 25, 2005
INVENTOR(S) : Mukund S. Chorghade et al.

It is certified that error appears in the above-identified patent and that said Letters Patent is hereby corrected as shown below:

Column 8,
Lines 55-60, please delete

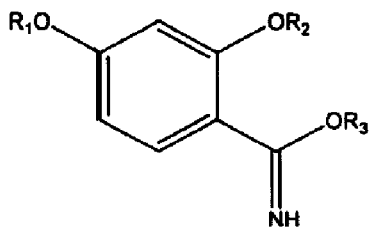

and insert

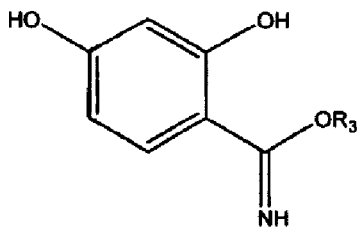

Signed and Sealed this

Seventeenth Day of May, 2005

JON W. DUDAS
*Director of the United States Patent and Trademark Office*